United States Patent
Kitagawa et al.

(10) Patent No.: US 11,045,574 B2
(45) Date of Patent: Jun. 29, 2021

(54) DEVICE AND PRODUCTION METHOD FOR THE SAME

(71) Applicant: Toray Industries, Inc., Tokyo (JP)

(72) Inventors: Rumiko Kitagawa, Otsu (JP); Masataka Nakamura, Otsu (JP)

(73) Assignee: Toray Industries, Inc., Tokyo (JP)

( * ) Notice: Subject to any disclaimer, the term of this patent is extended or adjusted under 35 U.S.C. 154(b) by 107 days.

(21) Appl. No.: 16/068,972

(22) PCT Filed: Feb. 22, 2017

(86) PCT No.: PCT/JP2017/006614
§ 371 (c)(1),
(2) Date: Jul. 10, 2018

(87) PCT Pub. No.: WO2017/146101
PCT Pub. Date: Aug. 31, 2017

(65) Prior Publication Data
US 2019/0015542 A1 Jan. 17, 2019

(30) Foreign Application Priority Data
Feb. 22, 2016 (JP) .............................. JP2016-030686

(51) Int. Cl.
| | | |
|---|---|---|
| A61L 15/24 | (2006.01) | |
| A61L 29/08 | (2006.01) | |
| A61L 31/10 | (2006.01) | |
| G02B 1/04 | (2006.01) | |
| A61L 31/04 | (2006.01) | |
| A61L 33/06 | (2006.01) | |
| B05D 7/24 | (2006.01) | |
| G02C 7/00 | (2006.01) | |
| A61L 27/34 | (2006.01) | |
| A61L 15/00 | (2006.01) | |
| B32B 27/30 | (2006.01) | |
| A61K 9/70 | (2006.01) | |
| B05D 1/18 | (2006.01) | |

(52) U.S. Cl.
CPC .............. *A61L 15/24* (2013.01); *A61K 9/70* (2013.01); *A61L 15/00* (2013.01); *A61L 27/34* (2013.01); *A61L 29/085* (2013.01); *A61L 31/04* (2013.01); *A61L 31/10* (2013.01); *A61L 33/06* (2013.01); *B05D 7/24* (2013.01); *B32B 27/30* (2013.01); *G02B 1/041* (2013.01); *G02B 1/043* (2013.01); *G02C 7/00* (2013.01); *B05D 1/18* (2013.01)

(58) Field of Classification Search
CPC . A61K 9/70; A61L 15/00; A61L 15/24; A61L 27/34; A61L 29/085; A61L 31/04; A61L 31/10; A61L 33/06; A61L 27/18; A61L 2400/10; A61L 2420/06; A61L 2430/16; A61L 27/50; A61L 27/52; B05D 1/18; B05D 7/24; B32B 27/30; G02B 1/041; G02B 1/043; G02C 7/00; B29D 11/00865
See application file for complete search history.

(56) References Cited

U.S. PATENT DOCUMENTS

| | | | |
|---|---|---|---|
| 8,480,227 B2 | 7/2013 | Qiu et al. | |
| 8,541,483 B2 | 9/2013 | Maggio et al. | |
| 8,591,950 B2 | 11/2013 | Bennett et al. | |
| 2002/0006521 A1* | 1/2002 | Shimoyama | ............... C08J 7/04 428/522 |
| 2004/0114105 A1 | 6/2004 | Shimoyama et al. | |
| 2012/0314183 A1 | 12/2012 | Nakamura et al. | |
| 2014/0198294 A1* | 7/2014 | Nakamura | ............. G02B 1/043 351/159.04 |
| 2015/0177417 A1* | 6/2015 | Nakamura | ................ A61F 2/14 351/159.33 |

FOREIGN PATENT DOCUMENTS

| | | |
|---|---|---|
| EP | 1153964 A2 | 11/2001 |
| EP | 2746835 A1 | 6/2014 |
| JP | 06287335 A | 10/1994 |
| JP | 2002047365 A | 2/2002 |
| JP | 2003171686 A | 6/2003 |
| JP | 2011246714 A | 12/2011 |
| JP | 2013533518 A | 8/2013 |
| WO | 0194454 A1 | 12/2001 |
| WO | 2013024799 A1 | 2/2013 |

OTHER PUBLICATIONS

International Search Report and Written Opinion for International Application No. PCT/JP2017/006614, dated Mar. 28, 2017—7 pages.
Extended European Search Report for European Application No. 17 756 539.7, dated Dec. 3, 2019, 8 pages.

* cited by examiner

*Primary Examiner* — Yan Lan
(74) *Attorney, Agent, or Firm* — RatnerPrestia

(57) ABSTRACT

Disclosed is a device including a substrate and a gel layer made of a hydrophilic polymer having a hydroxyl group. The gel layer is fixed to at least a part on a surface of the substrate in a thickness of 1 nm to 3,000 nm and an elastic modulus of a device surface is $6.00 \times 10^3$ Pa or less.

12 Claims, No Drawings

DEVICE AND PRODUCTION METHOD FOR THE SAME

CROSS REFERENCE TO RELATED APPLICATIONS

This is the U.S. National Phase application of PCT/JP2017/006614, filed Feb. 22, 2017, which claims priority to Japanese Patent Application No. 2016-030686, filed Feb. 22, 2016, the disclosure of these applications being incorporated herein by reference in their entireties for all purposes.

TECHNICAL FIELD OF THE INVENTION

The present invention relates to a hydrophilic device and a production method for the same.

BACKGROUND OF THE INVENTION

Heretofore, soft materials made of a resin such as a silicone rubber and hydrogel and hard materials such as metal and glass have been used for various purposes in various fields. Applications of soft materials include medical devices for introduction into a living body and for covering a surface of a living body, biotechnology devices such as cell culture sheets and scaffold materials for tissue regeneration, and cosmetic devices such as facial packs. Applications of hard materials include electric appliances such as personal computers, mobile phones, displays, etc., ampules for use in injections, and use as diagnostic and analysis tools such as capillaries, biosensing chips, and the like.

When various materials are introduced into a living body as a medical device or attached to a surface of a living body, in order to make it easy for adaptation to the living body, it becomes necessary to perform surface modification of materials for the purpose of improving hydrophilicity, lubricity, elasticity, and biocompatibility of the portion in contact with the living body. If it is possible to impart better hydrophilicity, lubricity, elasticity, and biocompatibility than before modification, users (patients, etc.) can expect an improvement in tactile sensation, reduction of discomfort, and the like. Various methods have been known as a method for modification of a surface of the material. For example, there has been known, as a method for hydrophilization of a surface of a hydrogel, a method in which a hydrophilic polymer is subjected to surface graft polymerization (see, for example, Patent Literature 1).

However, this method includes the steps of introducing a functional group having reactivity to both the hydrogel and the hydrophilic monomer into a surface of the hydrogel, and subjecting the hydrophilic monomer to surface graft polymerization, so that the production process may be prolonged to cause an increase in the production cost. Furthermore, applicable materials are limited to hydrous hydrogels.

Patent Literature 2 discloses a composite hydrogel composition which has appropriate elastic modulus and can be adjusted to various degrees of crosslinking by crosslinking hydrogels with each other. However, this method also requires the step of crosslinking two hydrogels after preparing each of two hydrogels, so that the production process may be prolonged to cause an increase in the production cost. Furthermore, applicable materials are limited to hydrous hydrogels.

Patent Literature

[Patent Literature 1] JP 6-287335 A
[Patent Literature 2] JP 2011-246714 A

SUMMARY OF THE INVENTION

The present invention has been made in view of foregoing circumstances, and it is an object of the present invention to provide a device whose surface has a moderate elastic modulus and is hydrophilized, and a method for simply producing the same.

To achieve the above object, the present invention has the following structures.

The present invention provides a device including a substrate and a gel layer made of a hydrophilic polymer having a hydroxyl group, and the gel layer is fixed to at least a part of the surface of the substrate in a thickness of 1 nm to 3,000 nm and an elastic modulus of the device surface is $6.00 \times 10^3$ Pa or less.

A method for producing the device according to the present invention includes disposing a substrate in a solution containing a hydrophilic polymer having a hydroxyl group adjusted to an initial pH of 2.3 or lower and heating the solution.

According to the present invention, it is possible to obtain a device in which moderate elastic modulus and hydrophilicity are imparted to a surface by a simple process. Applicable substrate is not limited to a hydrous hydrogel.

DETAILED DESCRIPTION OF EMBODIMENTS OF THE INVENTION

In the present invention, it is possible to use, as the substrate of the device, both a hydrous substrate and a non-hydrous substrate.

Specifically, the material of the hydrous substrate includes a hydrogel or the like. Examples of the material of the non-hydrous substrate include an acrylic resin such as polymethyl methacrylate, a silicone substrate having a siloxane bond, metal such as aluminum, and glass.

According to the present invention, it is possible to impart moderate elastic modulus and hydrophilicity to a surface of the device even if the substrate may be hydrous or non-hydrous. Therefore, the moisture content of substrate may be 0 to 99% by mass. The moisture content of the substrate is preferably 0.0001% by mass or more, and most preferably 0.001% by mass or more, since the effect of imparting moderate elastic modulus and hydrophilicity to the device surface is further enhanced. The moisture content of the substrate is preferably 50% by mass or less.

In the present invention, a gel layer is a layer in which a polymer is formed as a layer of a gel on a substrate surface. A part of the gel layer may enter into the inside of the substrate. "Gel" is usually used without being defined in academic papers and patent literature and is typically characterized by the fact that the polymer has high viscosity due to the network of a dispersoid to lose the fluidity, and thus the entire system becomes a solid state. Among the gels, a hydrogel containing water therein is preferable.

In the present invention, fixation means that the gel layer is fixed on a surface of the substrate through chemical bond such as hydrogen bond, ionic bond, van der Waals bond, hydrophobic bond, or complex formation. The gel layer may be fixed to the substrate through covalent bond, or rather, the gel layer is preferably fixed through hydrogen bond, ionic bond, van der Waals bond, hydrophobic bond, or complex formation since it becomes possible to produce by a simple process.

Depending on the application, the gel layer preferably exists on the entire surface of one surface of the substrate surface. In the case of a two-dimensional shape in which the substrate has no thickness or, if any, thickness can be neglected, the gel layer preferably exists on the entire surface of one surface of the substrate surface. More preferably, the gel layer exits on the entire surface of the substrate.

In the present invention, a gel layer made of a hydrophilic polymer exists while being fixed to a surface of the substrate. The material constituting the gel layer is usually a material different from that of the substrate. However, as long as a predetermined effect can be obtained, the material may be the same material as that constituting the substrate.

Here, the hydrophilic polymer is a polymer which is soluble in 100 parts by mass of water at room temperature (20 to 23° C.) in the amount of 0.0001 part by mass or more, preferably 0.01 part by mass or more, more preferably 0.1 part by mass or more, and still more preferably 1 part by mass or more, based on 100 parts by mass of water.

A hydrophilic polymer having a hydroxyl group is used as the hydrophilic polymer. The hydrophilic polymer having a hydroxyl group is preferable because it can form a surface excellent in not only water wettability but also antifouling properties against body fluid, and the like. The hydrophilic polymer having a hydroxyl group as used herein is preferably a polymer having an acidic hydroxyl group. Specifically, a polymer having a group selected from a carboxy group and a sulfonic acid group is preferable, and a polymer having a carboxy group is most preferable. The carboxy group or the sulfonic acid group may be in the form of a salt.

Examples of the hydrophilic polymer having a hydroxyl group include polymethacrylic acid, polyacrylic acid, poly(vinylbenzoic acid), poly(thiophene-3-acetic acid), poly(4-styrenesulfonic acid), polyvinylsulfonic acid, poly(2-acrylamido-2-methylpropanesulfonic acid), and salts thereof. Those mentioned above are examples of a homopolymer, and it is also possible to suitably use a copolymer of hydrophilic monomers constituting the hydrophilic polymer, or a copolymer of the hydrophilic monomer and the other monomer.

When the hydrophilic polymer having a hydroxyl group is a copolymer, the hydrophilic monomer constituting the copolymer is preferably a monomer having a group selected from an allyl group, a vinyl group, and a (meth)acryloyl group in view of high polymerizability. The monomer having a (meth)acryloyl group is most preferable. Suitable examples of such monomer include (meth)acrylic acid, vinylbenzoic acid, styrenesulfonic acid, vinylsulfonic acid, 2-acrylamido-2-methylpropanesulfonic acid, and salts thereof. Of these, a monomer selected from (meth)acrylic acid, 2-acrylamido-2-methylpropanesulfonic acid, and salts thereof is more preferable, and a monomer selected from (meth)acrylic acid and salts thereof is most preferable.

It is preferable that the hydrophilic polymer having a hydroxyl group has an amide group, in addition to the hydroxyl group, since it can form a surface having not only water wettability but also lubricity. Examples of the hydrophilic polymer having a hydroxyl group and an amide group include polyamides having a carboxyl group, a copolymer of a monomer having a hydroxyl group and a monomer having an amide group, and the like.

Suitable examples of the polyamides having a carboxyl group include polypeptides such as polyaspartic acid and polyglutamic acid, and polysaccharides such as hyaluronic acid and chondroitin sulfate.

Suitable examples of the monomer having a hydroxyl group include the monomers mentioned above. In view of ease of polymerization, the monomer having an amide group is preferably a monomer selected from a monomer having a (meth)acrylamide group and N-vinylcarboxylic acid amide (including cyclic one). Suitable Examples of such monomer include N-vinylpyrrolidone, N-vinylcaprolactam, N-vinylacetamide, N-methyl-N-vinylacetamide, N-vinylformamide, N,N-dimethylacrylamide, N,N-diethylacrylamide, N-isopropylacrylamide, N-(2-hydroxyethyl)acrylamide, acryloyl morpholine, and acrylamide. Of these, N-vinylpyrrolidone and N,N-dimethylacrylamide are preferable in view of the lubricity, and N,N-dimethylacrylamide is most preferable.

When the hydrophilic polymer having a hydroxyl group and an amide group is a copolymer, preferred specific examples are a (meth)acrylic acid/N-vinylpyrrolidone copolymer, a (meth)acrylic acid/N,N-dimethylacrylamide copolymer, a 2-acrylamido-2-methylpropanesulfonic acid/N-vinylpyrrolidone copolymer, and a 2-acrylamido-2-methylpropanesulfonic acid/N,N-dimethylacrylamide copolymer. A (meth)acrylic acid/N,N-dimethylacrylamide copolymer is most preferable.

When using a copolymer of a monomer having a hydroxyl group and a monomer having an amide group, the copolymerization ratio thereof is preferably in a range of 1/99 to 99/1 in terms of [mass of monomer having a hydroxyl group]/[mass of monomer having an amide group]. The copolymerization ratio of the monomer having a hydroxyl group is more preferably 2% by mass or more, still more preferably 5% by mass or more, and yet more preferably 10% by mass or more. The copolymerization ratio of the monomer having a hydroxyl group is more preferably 90% by mass or less, still more preferably 80% by mass or less, and yet more preferably 70% by mass or less. The copolymerization ratio of the monomer having an amide group is more preferably 10% by mass or more, still more preferably 20% by mass or more, and yet more preferably 30% by mass or more. The copolymerization ratio of the monomer having an amide group is more preferably 98% by mass or less, still more preferably 95% by mass or less, and yet more preferably 90% by mass or less. When the copolymerization ratio is within the above range, functions such as lubricity and antifouling properties against body fluid are easily developed.

In the above copolymer, it is also possible to copolymerize plural monomers having different hydroxyl groups and amide groups, or monomers having neither hydroxyl group nor amide group. It is also possible to use, as the monomer having neither hydroxyl group nor amide group, monomers exhibiting functions such as hydrophilicity, antibacterial property, and antifouling properties.

Various additives and the like can be included in the gel layer as long as they do not impair the properties required for the device. In addition to the hydrophilic polymer having a hydroxyl group, one or more other hydrophilic polymers having no hydroxyl group may be included in the gel layer. However, since the production method may be complicated, the gel layer is preferably composed of only one hydrophilic polymer having a hydroxyl group.

Here, one hydrophilic polymer means that the polymer is only a polymer or a polymer group (isomers, complexes, etc.) produced by one synthesis reaction. Even though the constituent monomer species is the same, when it contains plural copolymerized polymers synthesized with different compounding ratios, it is not said to be one polymer.

The expression that the gel layer is made of only one hydrophilic polymer having a hydroxyl group means that the gel layer does not contain any polymer other than the hydrophilic polymer having a hydroxyl group, or even if it contains the other polymer, it means that the content of the other polymer is 3 parts by mass or less based on 100 parts by mass of the hydrophilic polymer having a hydroxyl group. The content of the other polymer is more preferably 0.1 part by mass or less, and still more preferably 0.0001 part by mass or less.

In particular, when the other polymer is a basic polymer, if the content is more than the above range, a problem with transparency may occur. In the prior art, an acidic polymer and a basic polymer were used in combination to laminate a hydrophilic polymer on a surface of a substrate utilizing the electrostatic adsorption effect. However, according to the present invention, a gel layer made of only one hydrophilic polymer can be formed on a surface of the substrate.

If the moisture content change rate of the device due to the fixation of the gel layer is too small, it is impossible to impart satisfactory wettability and cushioning properties to the device, so that the moisture content change rate is preferably 10% by mass or more, more preferably 14% by mass or more, and still more preferably 20% by mass or more.

Here, the moisture content change rate (% by mass) of the device due to the fixation of the gel layer is calculated by determining a difference between the moisture content of the substrate before fixation of the gel layer and the moisture content of the substrate after fixation of the gel layer, which are measured by the method mentioned in Examples of the present specification. The moisture content change rate (% by mass) of the device due to the fixation of the gel layer is given by the following formula.

Moisture content change rate (% by mass) due to fixation of gel layer=moisture content (% by mass) of device after fixation of gel layer−moisture content (% by mass) of substrate before fixation of gel layer.

In the device of the present invention, since the gel layer is fixed to at least a part of a substrate surface, an elastic modulus of the device surface can be set at $6.00 \times 10^3$ Pa or less depending on the properties of the gel. The elastic modulus can be measured by a creep meter (e.g., high resolution type creep meter RE2-33005C (YAMADEN CORPORATION)). If the elastic modulus exceeds $6.00 \times 10^3$ Pa, when the device is used inside a living body, cushioning properties against the inner surface of the living body may deteriorate, leading to damage of the inner surface of the living body. Since moderate cushioning properties are exhibited to the inner surface of the living body, the elastic modulus is more preferably $5.00 \times 10^3$ Pa or less, and most preferably $4.00 \times 10^3$ Pa or less. The elastic modulus is more preferably $0.50 \times 10^2$ Pa or more, still more preferably $1.00 \times 10^2$ Pa or more, and most preferably $2.00 \times 10^2$ Pa or more.

Higher cushioning properties can be imparted to the substrate before the fixation of the gel layer, and when the device is used inside a living body, the inner surface of the living body is less likely to be damaged, so that the surface elastic modulus decrease rate (%) due to the fixation of the gel layer is preferably 50% or more, more preferably 70% or more, and most preferably 80% or more.

Here, the surface elastic modulus reduction rate (%) due to the fixation of the gel layer is given by the following formula.

Surface elastic modulus decrease rate of device due to fixation of gel layer (%)=(elastic modulus of substrate surface before fixation of gel layer−elastic modulus of device surface after fixation of gel layer)/elastic modulus of substrate surface before fixation of gel layer×100 (%).

When the device of the present invention is, for example, used inside a living body, it is difficult to damage an inner surface of the living body, so that the surface of the device preferably has excellent lubricity. An indicator representing the lubricity, the friction coefficient measured by the method mentioned in Examples of the present specification is preferably small. The friction coefficient is preferably 0.4 or less, more preferably 0.3 or less, still more preferably 0.2 or less, and most preferably 0.1 or less. If the friction coefficient is extremely small, it tends to be difficult to handle, so that the friction is preferably 0.0005 or more, and more preferably 0.001 or more.

When the device of the present invention is, for example, a medical device used to be stuck on a surface of a living body, liquid film retention time on the surface of the device is preferably long from the viewpoint of preventing from sticking to the skin of users. Here, the liquid film retention time is the time period during which a liquid film on the device surface is retained without being broken when the device immersed in a phosphate buffer solution is pulled up from the liquid and kept so that the surface is vertical in the air. The liquid film retention time is preferably 20 seconds or more, more preferably 60 seconds or more, and most preferably 100 seconds or more.

The total thickness of the gel layer is preferably 1 to 3,000 nm since it becomes easily to exhibit functions such as water wettability and cushioning properties. The thickness of the gel layer is more preferably 10 nm or more, still more preferably 20 nm or more since it is excellent in water wettability and cushioning properties, yet more preferably 50 nm or more, and most preferably 100 nm or more. As the gel layer becomes thicker, the more water wettability, lubricity, and cushioning properties of the surface are improved. The thickness of the gel layer is more preferably 2,000 nm or less, and still more preferably 1,000 nm or less. The thickness of the gel layer as used herein is the thickness of the gel layer observed using a transmission electron microscope in a cross section of the device in a dry state.

In preferred embodiment of the present invention, the device of the present invention may be in the form of a tube. Examples of the tubular device include an infusion tube, a gas delivery tube, a drainage tube, a blood circuit, a coating tube, a catheter, a stent, a sheath, a tube connector, an access port, and the like.

In another preferred embodiment of the present invention, the device of the present invention may be in the form of a sheet or a film. Specific examples thereof include a skin covering material, a wound dressing material, a protective material for skin, a drug carrier for skin, a biosensor chip, an endoscopic dressing material, and the like.

In still another preferred embodiment of the present invention, the device of the present invention may have a storage container shape. Specific examples thereof include a drug carrier, a cuff, a drainage bag, and the like.

In yet another preferred embodiment of the present invention, the device of the present invention may have a lens shape. Specific examples thereof include ophthalmic lenses such as intraocular lens, artificial cornea, corneal inlay, corneal onlay, eyeglass lens, and the like.

Next, a method of manufacturing a device of the present invention will be described. The device of the present invention can be obtained by a method in which a substrate is heated in a state of being disposed in a solution containing a hydrophilic polymer having a hydroxyl group.

Here, the inventors of the present invention have found that, using an extremely simple method in which an initial pH of the solution containing a hydrophilic polymer having a hydroxyl group is adjusted to 2.3 or lower and a substrate is disposed in the solution, and then the solution is heated in the state, the hydrophilic polymer having a hydroxyl group is fixed to a surface of the substrate as a gel layer, and thus the surface of the device can be brought into a state where the elastic modulus is $6.00 \times 10^3$ Pa or less, without using a conventionally known special method, for example, a method in which the electrostatic adsorption effect using an acidic polymer in combination with a basic polymer is utilized. Thereby, it is possible to impart excellent water wettability, cushioning properties, and the like to the device by a simple method, leading to industrially very important meaning from the viewpoint of shortening the production process.

The molecular weight of the hydrophilic polymer having a hydroxyl group can be changed in order to change various properties as a layer of the gel layer, for example, thickness. Increasing the molecular weight of the hydrophilic polymer generally increases the thickness of the resulting gel layer. However, when the molecular weight is too large, difficulty in handling during production may increase due to an increase in viscosity, so the hydrophilic polymer preferably has a molecular weight of 2,000 to 1,500,000. The molecular weight is more preferably 5,000 or more, and still more preferably 10,000 or more. The molecular weight is more preferably 1,200,000 or less, and still more preferably 1,000,000 or less. Here, the weight average molecular weight in terms of polyethylene glycol measured by a gel permeation chromatography method (aqueous solvent) is used as the molecular weight.

When the concentration of the hydrophilic polymer in the solution during production is increased, the thickness of the obtained gel layer increases. However, when the concentration of the hydrophilic polymer is too high, difficulty in handling during production may increase due to an increase in viscosity. Therefore, in the above process, the hydrophilic polymer having a hydroxyl group preferably has the concentration of 0.0001 to 30% by mass. The concentration of the hydrophilic polymer is more preferably 0.001% by mass or more, and still more preferably 0.005% by mass or more. The concentration is more preferably 20% by mass or less, and still more preferably 15% by mass or less.

In the above process, the initial pH value of the solution containing a hydrophilic polymer is preferably 2.3 or lower, more preferably 2.2 or lower, still more preferably 2.1 or lower, yet more preferably 2.0 or lower, most preferably 1.9 or lower, in order to obtain a gel layer such that the device surface excellent in cushioning properties exhibits an elasticity modulus of $6.00 \times 10^3$ Pa or less. The pH is preferably 0.1 or higher since it is easy to adjust the pH. When the initial pH is higher than 2.3, the elastic modulus of the formed gel layer may increase. For example, when the device is used inside a living body, cushioning properties against the inner surface of the living body may be insufficient depending on the application site. In that case, it is unfavorable since it may damage the inner surface of the living body.

The pH of the solution can be measured using a pH meter (e.g., pH meter Eutech pH 2700 (Eutech Instruments)). Here, the initial pH of a solution containing a hydrophilic polymer means the pH value of the solution measured after adding all the hydrophilic polymer to the solution, followed by stirring at room temperature (23 to 25° C.) for 2 hours with a rotor to thereby make the solution uniform, before disposing a substrate and heating the substrate. In the present invention, the pH value is rounded off to one decimal place.

The pH of the solution can change when a heating operation is performed. The pH of the solution after the heating operation is more preferably 0.1 to 5.0. The pH after heating is more preferably 0.5 or higher, and most preferably 1.0 or higher. The pH after heating is more preferably 4.5 or lower, and most preferably 4.0 or lower. When the pH of the solution after the heating operation is in the above range, appropriate pH conditions can be obtained while performing the heating operation, thus obtaining suitable physical properties. After modifying the device surface by performing the heating operation according to the present invention, the pH can be adjusted by performing a neutralization treatment or adding water. The pH of the solution after performing the heating operation is the pH before performing such pH adjustment.

A solvent of the solution containing a hydrophilic polymer having a hydroxyl group is preferably water. The pH of the solution is adjusted by adding an acidic substance such as acetic acid, citric acid, formic acid, ascorbic acid, trifluoromethanesulfonic acid, methanesulfonic acid, nitric acid, sulfuric acid, phosphoric acid, or hydrochloric acid to a solution containing a hydrophilic polymer. The acidic substance is not particularly limited as long as it can adjust the pH. To make it easy to finely adjust the pH, a buffering agent is preferably added to the solution.

It is possible to use, as the buffering agent, any physiologically compatible known buffering agent. Examples of buffering agent include boric acid, borate (e.g., sodium borate), citric acid, citrate (e.g., potassium citrate), bicarbonate (e.g., sodiumbicarbonate), phosphate (e.g., $Na_2HPO_4$, $NaH_2PO_4$, $KH_2PO_4$), TRIS (tris(hydroxymethyl) aminomethane), 2-bis(2-hydroxyethyl)amino-2-(hydroxymethyl)-1,3-propanediol, bis-aminopolyol, triethanolamine, ACES (N-(2-acetamide)-2-aminoethanesulfonic acid), BES (N,N-bis(2-hydroxyethyl)-2-aminoethanesulfonic acid), HEPES (4-(2-hydroxyethyl)-1-piperazineethanesulfonic acid), MES (2-(N-morpholino)ethanesulfonic acid), MOPS (3-[N-morpholino]-propanesulfonic acid), PIPES (piperazine-N,N'-bis(2-ethanesulfonic acid)), TES (N-[tris(hydroxymethyl)methyl]-2-aminoethanesulfonic acid), and salts thereof. The amount of the buffering agent is preferably 0.001% by mass to 2% by mass in the solution. The amount of the buffering agent is more preferably 0.01% by mass or more, and most preferably 0.05% by mass or more. The amount of the buffering agent is more preferably 1% by mass or less, and most preferably 0.30% by mass or less.

Examples of the heating method include a high-pressure steam sterilization method, irradiation with electromagnetic waves (γ ray, microwave, etc.), a dry heat method, a flame method, and the like. From the viewpoint of the water wettability, lubricity, and shortening of the production process, a high-pressure steam sterilization method is most preferable. An autoclave is preferably used as an apparatus.

The heating temperature is preferably 40° C. to 200° C. from the viewpoint of obtaining a device surface exhibiting satisfactory water wettability and lubricity and exerting less influence on the strength of the device itself. The heating temperature is more preferably 50° C. or higher, still more preferably 60° C. or higher, yet more preferably 80° C. or higher, further preferably 100° C. or higher, still further preferably 101° C. or higher, and most preferably 110° C. or higher. The heating temperature is more preferably 180° C. or lower, still more preferably 170° C. or lower, and most preferably 150° C. or lower.

If the heating time is too short, a device surface exhibiting satisfactory water wettability and lubricity cannot be obtained. Meanwhile, if the heating time is too long, an adverse influence is exerted on the strength of the device itself, the heating time is preferably 5 minutes to 600 minutes. The heating time is more preferably 10 minutes or more, and still more preferably 15 minutes or more. The heating time is more preferably 400 minutes or less, and still more preferably 300 minutes or less.

After the above heat treatment, the device thus obtained may be further subjected to the other treatment. Examples of the other treatment include treatments of methods such as a method in which a similar heat treatment is performed in a solution containing a hydrophilic polymer having a hydroxyl group, a method in which a similar heat treatment is performed by using a solution containing no hydrophilic polymer in place of the solution, a method in which irradiation with radiation is performed, a method of performing a layer by layer treatment (LbL treatment) in which each material having an opposite charge is alternately coated one by one, a method in which a crosslinking treatment with metal ions is performed, a method in which a chemical crosslinking treatment is performed, and the like. However, in light of the idea of the present invention which enables hydrophilization of a substrate surface by a simple method, a treatment is preferably performed as long as the production process does not become too complicated.

Radiations used for the above irradiation with radiation are preferably various ion beams, electron beams, positron beams, X-rays, γ rays, and neutron rays, more preferably electron rays and γ rays, and most preferably γ rays.

As the above LbL treatment, for example, a treatment using an acidic polymer and a basic polymer as mentioned in WO 2013/024800 A is preferably used.

Metal ions used for the above crosslinking treatment with metal ions are preferably various metal ions, more preferably monovalent and divalent metal ions, and most preferably divalent metal ions. Alternatively, a chelate complex may also be used.

As the above chemical crosslinking treatment, for example, a reaction between an epoxide group and a carboxyl group as mentioned in JP 2014-533381 A and a crosslinking treatment formed between known appropriate hydrophilic polymers having a hydroxyl group may be used.

In the above method in which a similar heat treatment is performed by using a solution containing no hydrophilic polymer in place of the solution, the solution containing no hydrophilic polymer is not particularly limited and a buffering agent solution is preferable. The above-mentioned substances can be used as the buffering agent.

The pH of the buffering agent solution is preferably within a physiologically acceptable range of 6.3 to 7.8. The pH of the buffering agent solution is preferably 6.5 or higher, and still more preferably 6.8 or higher. The pH of the buffering agent solution is preferably 7.6 or lower, and more preferably 7.4 or lower.

EXAMPLES

The present invention will be described more specifically by way of Examples, but the present invention is not limited to these Examples.
Analytical Method and Evaluation Method
<Water Wettability (Liquid Film Retention Time)>
A device was lightly washed in 100 mL of a phosphate buffer solution in a beaker at room temperature and then immersed in 100 mL of a fresh phosphate buffer solution for 24 hours or more. The device was pulled up from the phosphate buffer solution and the time during which the liquid film on the surface was retained in the case of keeping in the air was visually observed, and an average of N=3 was judged according to the following criteria.

A: A liquid film on a surface is retained for 100 seconds or more.
B: A liquid film on a surface disappears after 60 seconds or more and less than 100 seconds.
C: A liquid film on a surface disappears after 20 seconds or less than 60 seconds.
D: A liquid film on a surface disappears after 1 second or more and less than 20 seconds.
E: A liquid film on a surface instantly disappears (less than 1 second).
<Lubricity>
A device was lightly washed in 100 mL of a phosphate buffer solution in a beaker at room temperature and then immersed in 100 mL of a fresh phosphate buffer solution for 24 hours or more. The device was pulled up from the phosphate buffer solution and subjected to sensory evaluation when rubbing with a human finger five times (N=1).
A: There is extremely excellent lubricity (finger slides to flow on a device surface and feel no resistance).
B: There is lubricity intermediate between A and C.
C: There is moderate lubricity (finger slides on a device surface and hardly feels resistance).
D: Almost no lubricity (intermediate between C and E).
E: No lubricity (finger does not easily slide on a device surface and feel large resistance).
<Moisture Content of Substrate and Device>
A substrate was immersed in a phosphate buffer solution and left to stand at room temperature for 24 hours or more. The substrate was pulled out from the phosphate buffer solution and, after wiping off the surface moisture with a wiping cloth ("Kimwipes (registered trademark)" manufactured by NIPPON PAPER CRECIA CO., LTD.), the mass (Ww) of the substrate was measured. Thereafter, the substrate was dried at 40° C. for 2 hours in a vacuum dryer and the mass (Wd) was measured. From these masses, the moisture content of the substrate was calculated by the following formula (1). The case where the obtained value was less than 1% was judged as below the measurement limit, and the column in the table was filled with "less than 1%". An average of N=3 was regarded as the moisture content. The moisture content of the device after the fixation of the gel layer was also calculated in the same manner.

$$\text{Moisture content (\%) of substrate} = 100 \times (Ww - Wd)/Ww \quad \text{Formula (1)}$$

<Moisture Content Change Rate due to Fixation of Gel Layer>
The moisture content change rate was calculated by the following formula (2). An average of N=3 was regarded as the moisture content change rate due to the fixation of the gel layer.

$$\text{Moisture content change rate (\% by mass) due to fixation of gel layer} = \text{moisture content (\% by mass) of device after fixation of gel layer} - \text{moisture content (\% by mass) of substrate} \quad \text{Formula (2)}$$

<Molecular Weight Measurement>
The molecular weight of an acidic polymer used was measured under the following conditions.
(GPC Measurement Conditions)
Apparatus: Prominence GPC system manufactured by Shimadzu Corporation
Pump: LC-20AD
Autosampler: SIL-20AHT
Column oven: CTO-20A
Detector: RID-10A
Column: GMPWXL manufactured by Tosoh Corporation (7.8 mm in inner diameter×30 cm, particle diameter of 13 μm)

Solvent: water/methanol=1/1 (0.1 N lithium nitrate is added)
Flow rate: 0.5 mL/minute
Measurement time: 30 minutes
Sample concentration: 0.1% by mass
Injection amount: 100 μL
Standard sample: Polyethylene oxide standard sample manufactured by Agilent Technologies, Inc. (0.1 kD to 1258 kD)

<pH Measurement Method>

The pH of the solution was measured using a pH meter Eutech pH 2700 (Eutech Instruments). In Table 1, the initial pH of a solution containing a hydrophilic polymer having a hydroxyl group was determined by adding all the hydrophilic polymer to the solution mentioned in each Example, followed by stirring at room temperature (23 to 25° C.) for 2 hours with a rotor to thereby make the solution uniform. In Table 1, "pH after heat treatment" is the pH measured immediately after the solution was cooled to room temperature (23 to 25° C.) after a heat treatment was performed once.

<Measurement of Elastic Modulus of Device Surface>

The elastic modulus of the device surface after wiping off the surface moisture with a wiping cloth ("Kimwipes (registered trademark)" manufactured by NIPPON PAPER CRECIA CO., LTD.) was measured at three points under the following conditions, and an average of the initial elastic modulus during compression at each point calculated by the following formula (3) was regarded as the elastic modulus of the device surface.
Apparatus: High resolution type creep meter RE2-33005C (manufactured by YAMADEN Corporation)
Sample stand: Hemispherical top (diameter of 18 mm)
Load cell: 2 N full scale
Plunger: Φ mm
Compression speed: 0.05 mm/sec
Measurement environment: room temperature in atmospheric air Elastic modulus (Pa) of device surface=stress (Pa)/ strain (m)/device thickness (m))   Formula (3)

<Friction Coefficient>

The friction coefficient of the device surface wet with a phosphate buffer solution (preservation solution in a package for the measurement of a commercially available contact lens) under the following conditions was measured with N=5 and an average was regarded as the friction coefficient.
Apparatus: Friction tester KES-SE (manufactured by Kato Tech Co., Ltd.)
Friction SENS: H
Measurement SPEED: 2×1 mm/sec
Friction load: 44 g <Measurement of Film Thickness of Gel Layer>

The film thickness of a gel layer on a surface was measured by observing a cross section of a device in a dry state using a transmission electron microscope. While changing seven places, the film thickness was measured at five places for each field of view, and the film thickness was measured at 35 places in total. The minimum value and the maximum value of the measured film thickness are described.
Apparatus: Transmission electron microscope (H-7100FA manufactured by Hitachi, Ltd.)
Conditions: Acceleration voltage of 100 kV
Sample preparation: Method of staining ultrathin section with $RuO_4$.

[Reference Example 1]

After preparing 28 parts by mass of a polydimethylsiloxane having a methacryloyl group at both ends represented by the formula (M1) (FM 7726, JNC Corporation, Mw: 30,000), 7 parts by mass of a silicone monomer represented by the formula (M2), 57.9 parts by mass of trifluoroethyl acrylate ("Viscoat" (registered trademark) 3F, Osaka Organic Chemical Industry Ltd.), 7 parts by mass of 2-ethylhexyl acrylate (Tokyo Chemical Industry Co., Ltd.), and 0.1 part by mass of dimethylaminoethyl acrylate (Kohjin Co., Ltd.), preparing 5,000 ppm of a photoinitiator "IRGACURE" (registered trademark) 819 (NAGASE & CO., LTD.), 5,000 ppm of a UV absorber (RUVA-93, Otsuka Chemical Co., Ltd.), and 100 ppm of a colorant (RB 246, Arran chemical) based on the total amount of these monomers, and preparing 10 parts by mass of t-amyl alcohol based on 100 parts by mass of the total amount of these monomers, all components were mixed, followed by stirring. The mixture thus obtained by stirring was filtered through a membrane filter (pore diameter: 0.45 μm) to remove insoluble substances to obtain a monomer mixture.

The above monomer mixture was poured into a contact lens mold made of a transparent resin (material on base curve side: polypropylene, material on front curve side: polypropylene) and then polymerized by irradiation with light (wavelength 405 nm (±5 nm), illuminance: 0 to 0.7 $mW/cm^2$, for 30 minutes).

After the polymerization, the molded body thus obtained was immersed in an aqueous 100% by mass isopropyl alcohol solution at 60° C. for 1.5 hours together with the mold from which a front curve and a base curve were released, and then a molded body having a contact lens shape was removed from the mold. The molded body thus obtained was immersed in a large excess amount of an aqueous 100% by mass isopropyl alcohol solution maintained at 60° C. for 2 hours to extract impurities such as residual monomers. Thereafter, the molded body was dried at room temperature (23° C.) for 12 hours.

[Chemical Formula 1]

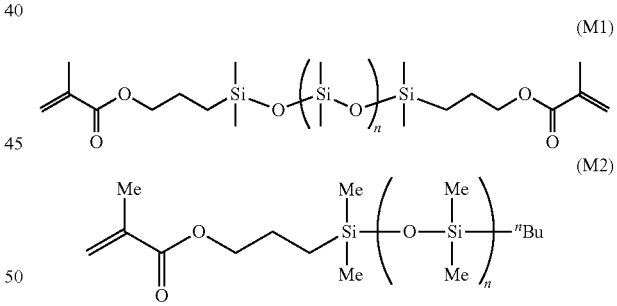

[Phosphate Buffer]

Each composition of the phosphate buffer solutions used in the processes of the following Examples and Comparative Examples and the above-mentioned measurements is as follows.
KCl: 0.2 g/L
$KH_2PO_4$: 0.2 g/L
NaCl: 8.0 g/L
$Na_2HPO_4$ (anhydrous): 1.15 g/L
EDTA: 0.25 g/L.

Example 1

A commercially available silicone hydrogel lens "Acuvue Oasys (registered trademark)" (manufactured by Johnson &

Johnson) containing polyvinylpyrrolidone and a silicone component was used as a substrate. The substrate was immersed in a solution containing 0.2% by mass of an acrylic acid/N,N-dimethylacrylamide copolymer (molar ratio in copolymerization: 1/9, Mw: 800,000, manufactured by Osaka Organic Chemical Industry Co., Ltd.) in pure water, which has the pH of 2.0 adjusted with sulfuric acid, followed by heating in an autoclave at 121° C. for 30 minutes. The molded body thus obtained was washed with a phosphate buffer solution while shaking at 250 rpm for 10 seconds. After replacing the phosphate buffer solution by a fresh phosphate buffer solution, the molded body was further heated in an autoclave at 121° C. for 30 minutes. The results obtained by evaluation of the molded body using the above method are shown in Table 2. A gel layer was confirmed on a surface of the molded body and the surface elastic modulus was low as shown in Table 2.

Example 2

In the same manner as in Example 1, except that a commercially available silicone hydrogel lens "1-Day Acuvue (registered trademark)" (manufactured by Johnson & Johnson) containing 2-hydroxyethyl methacrylate as a main component was used as the substrate, the treatment and evaluation were performed. The evaluation results are shown in Table 2. A gel layer was confirmed on a surface of the molded body and the surface elastic modulus was low as shown in Table 2.

Example 3

The molded body obtained in Reference Example 1 was used as a substrate. The substrate was immersed in a solution containing 0.03% by mass of an acrylic acid/N,N-dimethylacrylamide copolymer (molar ratio in copolymerization: 1/2, Mw: 800,000, manufactured by OSAKA ORGANIC CHEMICAL INDUSTRY LTD.) in pure water, which has the pH of 2.0 adjusted with sulfuric acid, followed by heating in an autoclave at 121° C. for 30 minutes. The molded body thus obtained was washed with a phosphate buffer solution while shaking at 250 rpm for 30 seconds. After replacing the phosphate buffer solution by a fresh phosphate buffer solution, the molded body was further heated in an autoclave at 121° C. for 30 minutes. The results obtained by evaluation of the molded body using the above method are shown in Table 2. A gel layer was confirmed on a surface of the molded body and the surface elastic modulus was low as shown in Table 2.

Example 4

The molded body obtained in Reference Example 1 was used as the substrate. The substrate was immersed in a solution containing 0.2% by mass of an acrylic acid/N,N-dimethylacrylamide copolymer in pure water, which is the same as in Example 1 and has the pH of 2.2 adjusted with sulfuric acid, followed by heating in an autoclave at 121° C. for 30 minutes. The molded body thus obtained was washed with a phosphate buffer solution while shaking at 250 rpm for 30 seconds. After replacing the phosphate buffer solution by a fresh phosphate buffer solution, the molded body was further heated in an autoclave at 121° C. for 30 minutes. The results obtained by evaluation of the molded body using the above method are shown in Table 2. A gel layer was confirmed on a surface of the molded body and the surface elastic modulus was low as shown in Table 2.

Example 5

The molded body obtained in Reference Example 1 was used as a substrate. The substrate was immersed in a solution containing 0.2% by mass of an acrylic acid/N,N-dimethylacrylamide copolymer in pure water, which is the same as in Example 1 and has the pH of 2.3 adjusted with sulfuric acid, followed by heating in an autoclave at 121° C. for 30 minutes. The molded body thus obtained was washed with a phosphate buffer solution while shaking at 250 rpm for 30 seconds. After replacing the phosphate buffer solution by a fresh phosphate buffer solution, the molded body was further heated in an autoclave at 121° C. for 30 minutes. The results obtained by evaluation of the molded body using the above method are shown in Table 2. A gel layer was confirmed on a surface of the molded body and the surface elastic modulus was low as shown in Table 2.

[Comparative Example 1]

The molded body obtained in Reference Example 1 was used as a substrate. The substrate was immersed in a solution containing 0.2% by mass of an acrylic acid/N,N-dimethylacrylamide copolymer in pure water, which is the same as in Example 1 and has the pH of 2.4 adjusted with sulfuric acid, followed by heating in an autoclave at 121° C. for 30 minutes. The molded body thus obtained was washed with a phosphate buffer solution while shaking at 250 rpm for 30 seconds. After replacing the phosphate buffer solution by a fresh phosphate buffer solution, the molded body was further heated in an autoclave at 121° C. for 30 minutes. The results obtained by evaluation of the molded body using the above method are shown in Table 2.

[Comparative Example 2]

The molded body obtained in Reference Example 1 was used as a substrate. The substrate was immersed in an aqueous solution (pH 2.6) containing 1.2% by mass of polyacrylic acid "Sokalan PA110S" (Mw: 250,000, manufactured by BASF), followed by heating in an autoclave at 121° C. for 30 minutes. The molded body thus obtained was washed with a phosphate buffer solution while shaking at 250 rpm for 30 seconds. After replacing the phosphate buffer solution by a fresh phosphate buffer solution, the molded body was further heated in an autoclave at 121° C. for 30 minutes. The results obtained by evaluation of the molded body using the above method are shown in Table 2.

[Comparative Example 3]

A commercially available silicone hydrogel lens "Acuvue Oasys (registered trademark)" (manufactured by Johnson & Johnson) containing polyvinylpyrrolidone and a silicone component was taken out from a package solution and then directly evaluated. The results obtained by evaluation of the molded body using the above method are shown in Table 2.

[Comparative Example 4]

A commercially available hydrogel lens "1-Day Acuvue (registered trademark)" (manufactured by Johnson & Johnson) containing 2-hydroxyethyl methacrylate as a main component was taken out from a package solution and then directly evaluated. The results obtained by evaluation of the molded body using the above method are shown in Table 2.

[Comparative Example 5]

The results obtained by directly evaluating the molded body obtained in Reference Example 1 are shown in Table 2.

[Comparative Example 6]

A commercially available silicone hydrogel lens "1-Day Acuvue TruEye (registered trademark)" (manufactured by Johnson & Johnson) containing polyvinylpyrrolidone and a silicone component was taken out from a package solution and then directly evaluated. The results obtained by evaluation of the molded body using the above method are shown in Table 2.

[Comparative Example 7]

A commercially available silicone hydrogel lens "AIR OPTIX (registered trademark) EX AQUA" (manufactured by Alcon Japan Ltd.) containing a silicone component, lens surface being subjected to a plasma treatment, was taken out from a package solution and then directly evaluated. The results obtained by evaluation of the molded body using the above method are shown in Table 2.

[Comparative Example 8]

A commercially available hydrogel lens "Proclear (registered trademark) 1 Day" (manufactured by Cooper Vision) containing 2-hydroxyethyl methacrylate copolymerized with an MPC monomer (2-methacryloyloxyethylphosphorylcholine) as a main component was taken out from a package solution and then directly evaluated. The results obtained by evaluation of the molded body using the above method are shown in Table 2.

[Comparative Example 9]

A commercially available silicone hydrogel lens "DAILIES TOTAL1 (registered trademark)" (manufactured by Alcon) containing a silicone component, two or more hydrophilic polymers being covalently bonded to lens surface, was taken out from a package solution and then directly evaluated. The results obtained by evaluation of the molded body using the above method are shown in Table 2.

TABLE 1

| | Substrate | Moisture content of substrate (%) | Hydrophilic polymer and concentration of solution thereof | Initial pH | pH after heating treatment |
|---|---|---|---|---|---|
| Example 1 | "Acuvue Oasys" | 38 | 0.2% by mass Acrylic acid/N,N-dimethylacrylamide copolymer | 2.0 | 2.3 |
| Example 2 | "1-Day Acuvue" | 58 | | 2.0 | 2.3 |
| Example 3 | Reference Example 1 | Less than 1% | 0.03% by mass Acrylic acid/N,N-dimethylacrylamide copolymer | 2.0 | 2.1 |
| Example 4 | Reference Example 1 | Less than 1% | 0.2% by mass Acrylic acid/N,N-dimethylacrylamide copolymer | 2.2 | 2.6 |
| Example 5 | Reference Example 1 | Less than 1% | | 2.3 | 3.3 |
| Comparative Example 1 | Reference Example 1 | Less than 1% | | 2.4 | 4.4 |
| Comparative Example 2 | Reference Example 1 | Less than 1% | 1.2% by mass Polyacrylic acid | 2.6 | 2.6 |
| Comparative Example 3 | "Acuvue Oasys" | 38 | None | None | None |
| Comparative Example 4 | "1-Day Acuvue" | 58 | None | None | None |
| Comparative Example 5 | Reference Example 1 | Less than 1% | None | None | None |
| Comparative Example 6 | "1-Day Acuvue Trueye" | 46 | None | None | None |
| Comparative Example 7 | "AIR OPTIX AQUA" | 24 | None | None | None |
| Comparative Example 8 | "Proclear 1 Day" | 60 | None | None | None |
| Comparative Example 9 | "DAILIES TOTAL1" | 33 | None | None | None |

TABLE 2

| | Liquid film retention time (seconds) | Lubricity | Surface elastic modulus (Pa) | Surface elastic modulus decrease rate due to fixation of gel layer (%) | Friction coefficient | Moisture content of device (%) | Moisture content change rate due to fixation of gel layer (%) | Film thickness of gel layer (nm) |
|---|---|---|---|---|---|---|---|---|
| Example 1 | A (120 seconds or more) | A | $8.06 \times 10^2$ | 87 | 0.006 | 62.6 | 24.6 | 210 to 319 |
| Example 2 | A (120 seconds or more) | A | $8.55 \times 10^2$ | 96 | 0.001 | 72.8 | 14.8 | 940 to 1,075 |
| Example 3 | A (120 seconds or more) | A | $2.64 \times 10^3$ | 98 | 0.025 | 29.8 | 29.8 | 100 to 207 |
| Example 4 | A (120 seconds or more) | A | $1.29 \times 10^3$ | 99 | 0.002 | 76.3 | 76.3 | 410 to 500 |
| Example 5 | A (120 seconds or more) | A | $9.91 \times 10^2$ | 99 | 0.001 | 75.1 | 75.1 | 400 to 510 |
| Comparative Example 1 | B (60 seconds) | A | $6.94 \times 10^3$ | 94 | 0.002 | 8.0 | 8.0 | 10 to 15 |
| Comparative Example 2 | E (0 second) | D | $1.12 \times 10^4$ | 91 | 0.579 | 0.1 | 0.1 | 0 |
| Comparative Example 3 | C (20 seconds) | C | $6.17 \times 10^3$ | None | 0.107 | 38 | 0 | 0 |
| Comparative Example 4 | C (20 seconds) | D | $1.96 \times 10^4$ | None | 0.434 | 58 | 0 | 0 |
| Comparative Example 5 | E (0 second) | E | $1.21 \times 10^5$ | None | 0.852 | Less than 1% | 0 | 0 |

TABLE 2-continued

|  | Liquid film retention time (seconds) | Lubricity | Surface elastic modulus (Pa) | Surface elastic modulus decrease rate due to fixation of gel layer (%) | Friction coefficient | Moisture content of device (%) | Moisture content change rate due to fixation of gel layer (%) | Film thickness of gel layer (nm) |
|---|---|---|---|---|---|---|---|---|
| Comparative Example 6 | D (3 seconds) | C | $3.62 \times 10^4$ | None | 0.190 | 46 | 0 | 0 |
| Comparative Example 7 | D (4 seconds) | D | $1.72 \times 10^4$ | None | 0.774 | 24 | 0 | 0 |
| Comparative Example 8 | D (4 seconds) | C | $1.70 \times 10^4$ | None | 0.321 | 60 | 0 | 0 |
| Comparative Example 9 | B (60 seconds) | A | $1.31 \times 10^4$ | None | 0.021 | 33 | 0 | 0* |

*Film thickness of a hydrophilic layer of the product itself is 100 to 200 nm.

The invention claimed is:

1. A device comprising a substrate and a gel layer made of only one hydrophilic polymer having a hydroxyl group, wherein the gel layer is fixed to at least a part on a surface of the substrate in a thickness of 100 nm to 3,000 nm and an elastic modulus of a device surface is $6.00 \times 10^3$ Pa or less, and wherein the gel layer contains 0.1 parts by mass or less of any other polymer that is not a hydrophilic polymer having a hydroxyl group and optionally an amide group based on 100 parts by mass of the hydrophilic polymer.

2. The device according to claim 1, wherein the hydrophilic polymer has an amide group.

3. The device according to claim 1, wherein liquid film retention time is 20 seconds or more.

4. The device according to claim 3, wherein liquid film retention time is 60 seconds or more.

5. The device according to claim 1, wherein a friction coefficient of the device surface is 0.4 or less.

6. The device according to claim 1, which is a medical device.

7. The device according to claim 1, which is an ophthalmic lens, a dermal covering material, a wound dressing material, a skin protection material, a skin medicine carrier, an infusion tube, a gas delivery tube, a drain tube, a blood circuit, a covering tube, a catheter, a stent, a sheath, a tube connector, an access port, a biosensor chip, or an endoscopic dressing material.

8. A method for producing a device, which comprises disposing a substrate in a solution containing a hydrophilic polymer having a hydroxyl group adjusted to an initial pH of 2.3 or lower and the substrate is heated at 100° C. or higher in a state of being disposed in the solution containing a hydrophilic polymer having a hydroxyl group.

9. The method for producing a device according to claim 8, wherein the heating is performed in an autoclave.

10. The method for producing a device according to claim 8, wherein the device before and after heating has a moisture content change rate of 10% by mass or more.

11. The method for producing a device according to claim 8, wherein the initial pH is 1.9 or lower.

12. A method for producing a device, which comprises disposing a substrate in a solution containing a hydrophilic polymer having a hydroxyl group adjusted to an initial pH of 2.3 or lower and heating the solution to obtain a device comprising a substrate and a gel layer made of only one hydrophilic polymer having a hydroxyl group, wherein the gel layer is fixed to at least a part on a surface of the substrate in a thickness of 100 nm to 3,000 nm and an elastic modulus of a device surface is $6.00 \times 10^3$ Pa or less.

* * * * *